United States Patent [19]
Linder

[11] Patent Number: 5,643,230
[45] Date of Patent: Jul. 1, 1997

[54] NASOGASTRIC SUCTION CATHETER

[76] Inventor: Gerald Seymour Linder, 16693 Charmel La., Pacific Palisades, Calif. 90272

[21] Appl. No.: 441,548

[22] Filed: May 15, 1995

[51] Int. Cl.⁶ .......................... A61M 5/00; A61M 25/00
[52] U.S. Cl. .................................. 604/280; 604/264
[58] Field of Search .............................. 604/264, 270, 604/280, 282, 284, 43, 902

[56] References Cited

U.S. PATENT DOCUMENTS

| | | | |
|---|---|---|---|
| 3,982,540 | 9/1976 | Ross | 128/278 |
| 4,182,342 | 1/1980 | Smith | 128/348 |
| 4,735,607 | 4/1988 | Keith, Jr. | 604/54 |
| 4,867,747 | 9/1989 | Yarger | 604/263 |

*Primary Examiner*—Robert A. Hafer
*Assistant Examiner*—Deborah B. Blyveis
*Attorney, Agent, or Firm*—B. F. Spencer

[57] ABSTRACT

A nasogastric suction catheter is disclosed consisting of a long, slender, flexible tube member having independent suction and vent lumens, both lumens being open at both the proximal and distal ends of the long, flexible tube member. The open proximal end of the suction lumen of the long, flexible tube is adapted for coupling to the conventional suction pump. The open distal end of the long, flexible tube is provided with a short, soft, hollow distal end member securely bonded thereto. The short, soft, hollow distal end member is provided with a number of spaced-apart, longitudinally extending ridges located upon its outer surface, with the space between adjacent, parallel ridges forming longitudinally extending troughs. A number of spaced-apart suction apertures are located between the parallel, extended ridges and through the bottom of the troughs into the short, hollow distal end member. When the short, soft distal end member of the nasogastric suction catheter is intubated within the stomach of a patient and a suctioning force is applied to the suction lumen of the catheter at its proximal end, the contents of the stomach of the patient are drawn into the several troughs and through the suction apertures into the hollow distal end member and out through the suction lumen of the suction catheter.

9 Claims, 1 Drawing Sheet

NASOGASTRIC SUCTION CATHETER

BACKGROUND OF THE INVENTION

The present invention relates to suction catheters and, in particular, to nasogastric suction catheters for withdrawing the contents of the stomach of the patient.

The conventional nasogastric suction catheter of the prior art consists of a long, slender, hollow, flexible tube having a primary suction lumen and a smaller vent lumen. The two lumens are separate and independent from each other. The proximal end of the nasogastric suction catheter is open and is provided with spaced-apart independent couplings, one for the suction lumen and the other for the vent lumen. The coupling for the suction lumen is frequently enlarged and is designed for attachment to the hose of the conventional suction pump. The coupling for the vent lumen may be open to air at atmospheric pressure, or it may be coupled to a reflux valve.

The distal end portion of one representative nasogastric suction catheter is provided with a plurality of openings or suction apertures extending from the suction lumen out through the cylindrical walls of the long, slender, hollow flexible tube to the outside surface of the flexible tube. These suction apertures can vary both in number and size, a typical suction catheter having from six to ten apertures, equally divided on opposite sides of the distal end portion. The length of the distal end portion, with its several suction apertures, may vary from approximately one to three inches, depending in part upon the size and length of the suction catheter and upon the age and size of the patient for which the catheter is to be used.

The distal tip of the conventional nasogastric suction catheter is sealed closed and rounded smooth to aid its intubation through the naris, the esophagus and into the stomach of the patient. The distal end of the vent lumen is open, and the opening may be internal, inside the suction lumen, or both internal and external of the suction lumen. The function of the vent lumen is to allow air to pass from the open proximal end of the suction catheter down through the vent lumen into the stomach of the patient as the contents of the stomach are being withdrawn up through the suction lumen. Additionally, the vent lumen, as well as the suction lumen, can be used as an irrigation lumen to introduce a fluid, such as a saline solution, into the stomach of the patient to aid in flushing residual matter needed to be withdrawn.

The suction apertures of the conventional nasogastric suction catheter usually are punched through the cylindrical wall of the distal end portion and into the suction lumen by a sharp hole-cutting punch. These suction apertures may be oval or circular in shape. The cutting of the suction apertures by the punch leaves sharp edges at the cylindrical surface around the peripheries of the apertures. These sharp peripheral edges are known to cause injury to the patient during both the intubation as well as the suctioning procedures as these apertures rub against the sensitive membranes and linings of the naris, the esophagus, and the inner walls of the stomach. Additionally, as the walls of the stomach begin to collapse as the contents are being withdrawn, the mucosa of the stomach is susceptible to being drawn into the suction apertures, thereby occluding the apertures and causing additional trauma to the patient.

Since the distal end portion of the conventional nasogastric suction catheter is formed at the distal end of the long, slender, hollow flexible tube, the rounded and closed distal tip is of the same material and texture as the long, slender, flexible tube. This distal tip, though rounded smooth, is relatively hard due to the heating and forming required to seal and round the tip during manufacture.

As the distal end portion, with its distal tip, must of necessity be intubated within the stomach, any forceful engagement of the distal tip against the inner walls of the stomach results in trauma to the patient. Because force is required to intubate nasogastric suction catheters, the using physician must exercise due care to properly position the distal end portion within the stomach to minimize trauma.

BRIEF SUMMARY OF THE INVENTION

The present invention introduces an improved nasogastric suction catheter to minimize and alleviate the above-mentioned problems by employing a short, hollow distal end member having a different physical shape and configuration and being composed of material that is both soft and resilient. The short, soft, hollow distal end member is shaped, as by molding, to include a number of spaced-apart, longitudinally extending ridges upon its outer surface. The space between the adjacent, parallel ridges forms the side walls of troughs, the troughs extending for the lengths of the ridges and are open at their ends. The spaced-apart suction apertures of the improved nasogastric catheter are located through the bottom of the troughs and into the hollow distal end member. These suction apertures are between the side walls of the adjacent, longitudinally extending ridges and below the crest of the ridges. These ridges, with their side walls, serve to prevent the linings and inner walls of the naris, esophagus and stomach from engaging the suction apertures during the intubation and the suctioning procedures.

The short, soft, hollow distal end member of the invention is made opaque to x-rays by the addition of a small percentage of the compound barium sulfate to the polyvinylchloride powder from which the distal end member is manufactured, as by molding under heat and pressure.

Accordingly, it is a primary object of the invention to provide an improved nasogastric suction catheter capable of reducing injury to the patient during the intubation and the suctioning procedures.

An important object of the invention is to provide a nasogastric suction catheter wherein the apertures within the soft, hollow distal end of the catheter are prevented from engaging and injuring the mucosa of the stomach of the patient during the suctioning procedure.

Another object is to provide an improved nasogastric suction catheter having a distal end member that is opaque to x-rays to aid the using physician in properly positioning the distal end portion within the stomach of the patient.

The above objects of and the brief introduction to the present invention will be more fully understood, and further objects and advantages will become apparent, from a study of the following detailed description in connection with the drawings.

DESCRIPTION OF THE INVENTION

Figure 1:
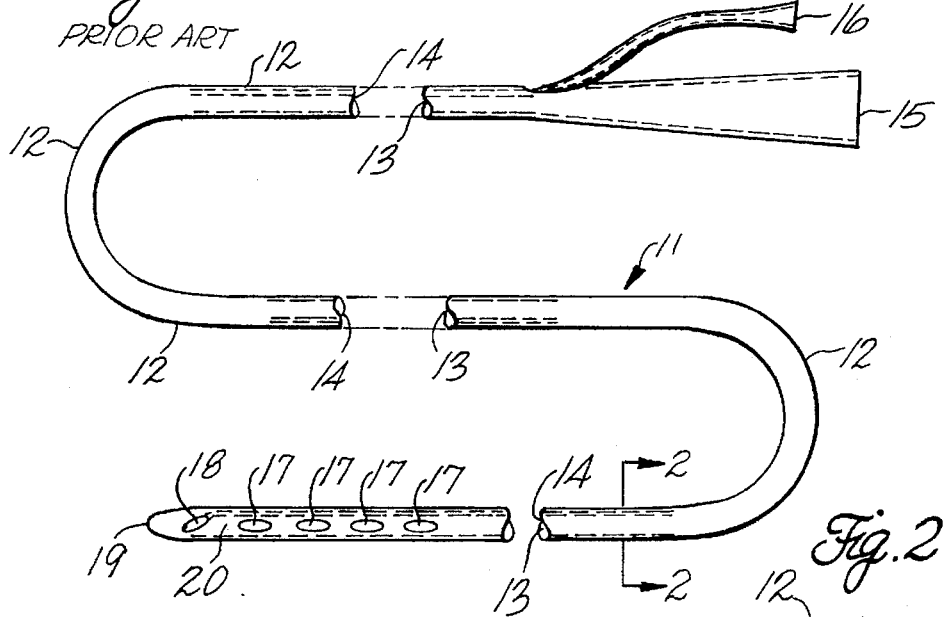
FIG. 1 is a side view of a conventional prior art nasogastric suctiom catheter.

The conventional nasogastric suction catheter 11 of FIG. 1 consists of a long, slender, hollow, flexible tube 12 having a primary suction lumen 13 and a smaller vent lumen 14. The vent lumen 14 is identified by the close-spaced parallel broken lines inside the outer surface of flexible tube 12. The two lumens 13 and 14 are separate and independent from each other and extend for the full length of flexible tube 12. The proximal end 15 of suction lumen 13 is enlarged and is open as shown. The proximal end 16 of the smaller vent lumen 14 is separated from the proximal end 15 to allow independent coupling to these two lumens. The conventional suction pump is coupled, by a suction hose, to proximal end 15.

The distal end portion of suction catheter 11 is provided with a group of four suction apertures 17 punched through outer surface 20 of flexible tube 12 into suction lumen 13. An additional group of four suction apertures 17 are also punched on the opposite side of flexible tube 12 through outer surface 20 of flexible tube 12 into the suction lumen. The two groups of apertures 17 are punched through the outer surface 20 of flexible tube 12 without rupture or penetration of vent lumen 14. Apertures 17 can be either oval or circular in shape.

Aperture 18, located near rounded distal tip 19, is punched through the outer surface 20 of flexible tube 12 into both suction lumen 13 and vent lumen 14. An additional aperture 18 is also punched on the opposite side of flexible tube 12 through the outer surface 20 into lumens 13 and 14. Aperture 18 permits air entering the proximal end 16 of nasogastric suction catheter 11 to exit both into suction lumen 13 and out through aperture 18 into the area surrounding the distal end portion of the catheter.

Nasogastric suction catheter 11 of FIG. 1 is manufactured from medically approved polyvinylchloride tubing, and the illustration in FIG. 1 is approximately to scale for a conventional size 16 French suction catheter, which employs a flexible tube having an outer diameter of approximately six millimeters.

Figure 2:
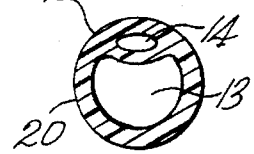
FIG. 2 is an enlarged cross-sectional view taken along the lines 2—2 of the long, slender, flexible tube of the prior art nasogastric suction catheter of FIG. 1 showing the main suction lumen and the secondary vent lumen.

The cross-sectional view of flexible tube 12 in FIG. 2 is enlarged approximately two and one-half times that of FIG. 1 to better illustrate the configuration and relative sizes of suction lumen 13 and smaller vent lumen 14.

Figure 3:
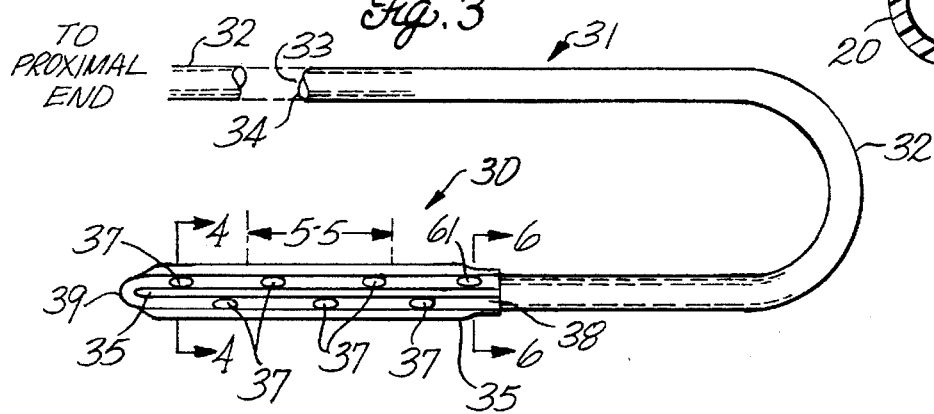
FIG. 3 is a side view of the nasogastric suction catheter of the invention showing the short, hollow distal end member attached to the open distal end of the long, slender, flexible tube of the suction catheter.

FIG. 3 illustrates improved nasogastric suction catheter 31 of the invention consisting of a long, slender, hollow, flexible tube 32 composed of medically approved polyvinylchloride tubing having suction lumen 33 and vent lumen 34. Flexible tube 32 may be identical to that of flexible tube 12 of FIG. 1. The open proximal end (not shown) of flexible tube 32 is identical to that illustrated in FIG. 1 including separate and independent couplings for the two lumens 33 and 34.

Figure 4:
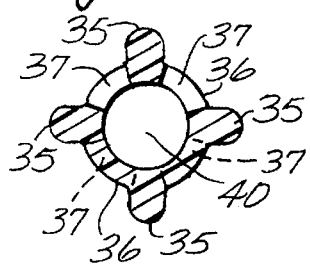
FIG. 4 is an enlarged cross-sectional view taken along the lines 4—4 of the short, hollow distal end member of FIG. 3.
Figure 5:
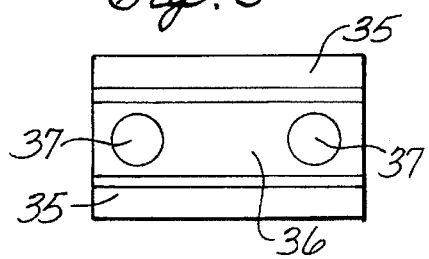
FIG. 5 is an enlarged view of the central portion of the short, hollow distal end member of FIG. 3 taken between the parallel lines 5—5, this central portion being rotated forty-five degrees about the longitudinal axis of the distal end member to illustrate the suction apertures located in the bottom of the trough formed by the walls of the adjacent parallel ridges.

Referring to FIGS. 3, 4 and 5, a short, soft, hollow distal end member 30 is attached to the distal end of flexible tube 32 of suction catheter 31. Distal end member 30 is provided with four spaced-apart, longitudinally extending ridges 35 distributed around its cylindrical outer surface, as best illustrated in the enlarged cross-sectional view of FIG. 4. Ridges 35 are parallel to each other and are tapered at their ends, as shown in FIG. 3. The space lying between adjacent, parallel ridges 35 forms a group of four troughs 36 extending for the lengths of ridges 35, troughs 36 being open at each of their ends, as illustrated in FIG. 4.

A group of three spaced-apart suction apertures 37 are located between each of the adjacent, parallel ridges 35 and in the bottom of each of the troughs 36, as seen in FIGS. 3 and 4. Apertures 37 extend through the bottom of troughs 36 into cylindrical lumen 40 of distal end member 30. Apertures 37 are the passageways for receiving the contents of the stomach of the patient to be withdrawn, such contents passing through cylindrical lumen 40 into suction lumen 33 and up flexible tube 32 to the proximal end of suction catheter 31.

Figure 6:
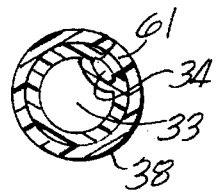
FIG. 6 is an enlarged cross-sectional view of the proximal end of the short, hollow distal end member of FIG. 3 taken along the lines 6—6 to illustrate the small opening extending from the vent lumen through the wall of the flexible tube to the outside surface of the proximal end of the short, hollow distal end member.

The views of the parts of distal end member 30, shown in FIGS. 4, 5 and 6, are enlarged approximately three times normal size to better illustrate the configuration of distal end member 30. Two of the spaced-apart apertures 37, circular in shape, are shown in FIG. 5 at the bottom of trough 36, trough 36 being formed between the parallel side walls of the two ridges 35. The diameters of circular apertures 37 are smaller than the cross-sectional diameter of suction lumen 33.

Referring to FIGS. 3 and 6, the open distal end of flexible tube 32 extends into cylindrical lumen 40 of distal end member 30, thereby enabling air from vent lumen 34 to exit into lumen 40 and out through any of suction apertures 37 to the outside area surrounding distal end member 30. An additional exit is provided for air to escape from vent lumen 34 by way of small opening 61 extending from vent lumen 34 through the wall of flexible tube 32 and through the wall of proximal end 38 of distal end member 30, as seen in FIG. 6.

Distal end member 30 of the invention is manufactured by injection molding under heat and pressure from a batch of small pellets of polyvinylchloride. The small pellets themselves are made by an extrusion process from polyvinylchloride powder and a selected liquid softening agent or plasticizer. The proportions of polyvinylchloride powder and the softening agent determine the softness and resilience of the extruded pellets. The extruded pellets will have a latex, rubber-like texture to assure that molded distal end member 30 will possess the softness and resilience desired.

The batch of small pellets of polyvinylchloride may contain a selected pigment before distal end member 30 is manufactured within the injection mold to give it a distinctive color.

The distal end member 30 of the invention contains an added chemical compound of barium sulfate mixed with the batch of polyvinylchloride pellets to render distal end member 30 x-ray opaque. Approximately five to ten percent barium sulfate to ninety percent pellets has been found satisfactory for this purpose. Since barium sulfate is white in color, it may serve as a selected pigment to render distal end member 30 distinct from the clear, transparent polyvinylchloride flexible tube 32.

While molded distal end member 30 is soft, resilient and somewhat stretchable, like latex rubber, the spaced-apart, longitudinally extended ridges 35 provide a certain amount of resistance to bending by virtue of the width and height of these ridges, as can be seen in FIG. 4. The using physician, under acceptable medical practice, will apply a water soluble lubricant to the selected sterilized nasogastric suction catheter, including its distal end portion, to assist intubation through the naris, esophagus and into the stomach. The lubricated crests of ridges 35, while physically engaging the linings of the naris and esophagus and the mucosa of the stomach, during intubation, serve to restrain and prevent these linings and mucosa from physical contact with the edges of suction apertures 37, thereby reducing trauma to the patient.

Since many changes may be made in the above described device and many different embodiments of this invention could be made without departing from the scope thereof, it is intended that all matter contained in the above description or shown in the accompanying drawings shall be interpreted as illustrative and not in a limiting sense.

What is claimed is:

1. A nasogastric suction catheter comprising in combination:

(a) a long, slender, flexible tube member having open proximal and distal ends, said flexible tube member having a main suction lumen and a secondary vent lumen, said lumens extending the entire length of said flexible tube member and being separate and independent one from the other;

(b) means formed at the proximal end of said flexible tube member for providing spaced-apart and independent couplings to said suction and vent lumens;

(c) a short, soft, hollow distal end member having an open proximal end bonded to the distal end of said long, flexible tube member, said hollow distal end member having a cylindrical lumen with a diameter approximately equal to the outer diameter of the distal end of said flexible tube member, said hollow distal end member having a plurality of longitudinally extending and spaced-apart ridges upon the outer surface thereof, said plurality of spaced-apart ridges being parallel to each other, the space lying between said spaced-apart, parallel ridges and on the outer surface of said hollow distal end member forming troughs between said ridges, said troughs being open at each of their ends, said short, soft, hollow distal end member having a soft, rounded distal tip, said short, soft, hollow distal end member, including said soft, rounded distal tip being appreciably softer and more resilient than said long, slender, flexible tube member; and (d) a plurality of longitudinally spaced-apart suction apertures located between said parallel ridges and within the troughs of said soft, hollow distal end member, said plurality of apertures extending through the bottom of said troughs into the cylindrical lumen of said soft, hollow distal end member.

2. The nasogastric suction catheter as defined by claim 1 wherein said short, soft, hollow distal end member is molded of polyvinylchloride having a stretchable, rubber-like texture.

3. The nasogastric suction catheter as defined by claim 1 wherein each of said plurality of longitudinally spaced-apart suction apertures is circular in shape, and wherein the diameters of each of said circular-shaped apertures is less than the cross-sectional diameter of the main suction lumen of said long, slender, flexible tube member.

4. The nasogastric suction catheter as defined by claim 1 wherein said long, slender, flexible tube member and said short, soft, hollow distal end member are both composed of polyvinylchloride.

5. The nasogastric suction catheter as defined by claim 1 wherein said short, soft, hollow distal end member is composed of a mixture of polyvinylchloride and an x-ray opaque compound, of barium sulfate said mixture rendering said short, soft, hollow distal end member partially opaque to the passage of x-rays.

6. The nasogastric suction catheter as defined by claim 1 wherein said secondary vent lumen at the open distal end of said long, slender flexible tube opens into the hollow cylindrical lumen of said short, hollow distal end member.

7. The nasogastric suction catheter as defined by claim 1 further comprising a small opening near the distal end of said long, slender, flexible tube member extending radially from within said secondary lumen out through the cylindrical wall of said long, flexible tube member to its outside surface.

8. The nasogastric suction catheter as defined by claim 1 wherein each of said plurality of longitudinally spaced-apart apertures is circular in shape, and wherein the diameter of each of said circular-shaped apertures is approximately equal to the width of the bottom of said troughs.

9. The nasogastric suction catheter as defined by claim 1 wherein each end of each of said plurality of spaced-apart ridges has a gradual diminution in height, as by tapering, thereby providing a leading and a trailing inclined surface to the opposite ends of each of said spaced-apart ridges.

* * * * *